United States Patent [19]

Tsuchiko et al.

[11] Patent Number: 5,251,631
[45] Date of Patent: Oct. 12, 1993

[54] ULTRASONIC IMAGING APPARATUS

[75] Inventors: Masayoshi Tsuchiko, Tochigi; Hiromi Maekawa; Kazunari Nakata, both of Ootawara, all of Japan

[73] Assignee: Kabushiki Kaisha Toshiba, Kawasaki, Japan

[21] Appl. No.: 788,473

[22] Filed: Nov. 6, 1991

[30] Foreign Application Priority Data

Nov. 7, 1990 [JP] Japan ................. 2-301343

[51] Int. Cl.$^5$ .............................................. A61B 8/00
[52] U.S. Cl. ..................................................... 128/661.01
[58] Field of Search ..................... 128/661.01, 660.01, 128/662.03; 73/625-626

[56] References Cited

U.S. PATENT DOCUMENTS

| | | | |
|---|---|---|---|
| 4,446,715 | 5/1984 | Bailey | 364/571 |
| 4,811,740 | 3/1989 | Ikeda et al. | 128/660.01 |
| 5,129,397 | 7/1992 | Jingu et al. | 128/660.01 |

Primary Examiner—Francis Jaworski
Attorney, Agent, or Firm—Finnegan, Henderson, Farabow, Garrett & Dunner

[57] ABSTRACT

An ultrasonic imaging apparatus comprising the main body containing a transmission system, a reception system composed of a plurality of receiving sections, a signal processing system, a display system, and a first connector, a probe unit containing a plurality of transducers, a second connector for connecting the probe unit to the first connector of the main body in a detachable manner, a memory in stalled in the second connector for storing data to calibrate at least one of the sensitivity and phase characteristics for each of the plurality of transducers, and a calibration circuit installed in the main body for retrieving stored data from the memory and calibrating one of sensitivity and phase characteristics for each of the plurality of receiving sections of the reception system.

12 Claims, 11 Drawing Sheets

ULTRASONIC IMAGING APPARATUS

BACKGROUND OF THE INVENTION

1. Field of the Invention

This invention relates to an ultrasonic imaging apparatus such as a medical electronic-scanning ultrasonic diagnostic apparatus.

2. Description of the Related Art

For medical electronic-scanning ultrasonic diagnostic apparatus, various types of ultrasonic probe units are used depending on clinical and/or technical conditions. Typical examples of clinical conditions include the shape and location of a visual field region or a target region. Typical examples of technical conditions include the number of arrays of transducers and the natural frequency of each transducer. According to the clinical and/or technical conditions required by the operator, a diagnostic format, such as B-mode display (tomographic image display), M-mode display (motion image display), D-mode display (Doppler image display), BDF-mode display (superposed display of a tomographic image and a flow mapping image), MDF-mode display (superposed display of a motion image and a color mapping image), linear scanning, sector scanning, and convex scanning, is carried out.

The probe unit used in such an ultrasonic imaging apparatus as a medical electronic-scanning ultrasonic diagnostic apparatus contains a transducer section consisting of arrays of transducers. This transducer section is applied to the subject. When the transmission system is activated, the transducer section transmits an ultrasonic beam to the subject and then receives reflected waves generated within the subject. Based on the received waves, the transducer section produces and supplies a reception signal to the reception system. The transmission system and reception system are based on scanning control such as electrical scanning. The reception signal entering the reception system is processed at the signal processing system to produce display information such as a tomographic image.

In the above medical electronic-scanning ultrasonic diagnostic apparatus, electronic scanning control and beam deflection control are achieved by performing the transmission driving and reception driving of the arrays of transducers in the transducer section, each transducer being assigned a different amount of delay. Such control is known as phase control. Since electronic ultrasonic scanning provides phase control of arrays of transducers, scanning control accuracy and display information precision are dependent largely on the phase characteristics of the transducer section. The transducer section composed of transducers of identical characteristics arranged with high accuracy would provide excellent phase characteristic. In the manufacture of actual transducers, however, it is natural that there is a limit to obtaining a plurality of transducers of identical characteristics and arranging them with high accuracy. As a consequence, it has been impossible to obtain satisfactory ultrasonic images.

The operating conditions such as an excitation frequency vary with the type of a probe unit used. In addition, as mentioned above, the transducers constituting the transducer section each have different phase characteristics. Therefore, for example, when a tomographic image is displayed with the main body connected to a linear scanning probe unit and then to another different in the specifications from the first, no satisfactory ultrasonic image is obtainable even if a specified excitation frequency is set for each case, because the probe units differ from each other in terms of phase characteristics.

SUMMARY OF THE INVENTION

Accordingly, the object of the present invention is to provide an ultrasonic imaging apparatus capable of providing good ultrasonic information.

The foregoing object is accomplished by providing an ultrasonic imaging apparatus comprising: the main body containing at least a transmission system, a reception system composed of a plurality of receiving sections, a signal processing system, a display system, and a first connector; probe means containing a plurality of transducers; a second connector for connecting the probe means to the first connector of the main body in a detachable manner; data storage means installed in the second connector for storing data on the transducer channel parameter for each of the plurality of transducers; and calibration means installed in the main body for retrieving stored data from the data storage means and calibrating the receiving channel parameter for each of the plurality of receiving sections of the reception system.

The foregoing object is also accomplished by providing an ultrasonic imaging apparatus comprising: the main body containing at least a transmission system, a reception system composed of a plurality of receiving sections, a signal processing system, and a display system; data storage means installed in the main body for storing data on the transducer channel parameter for each of the plurality of transducers of at least one probe means; probe means containing a plurality of transducers, which is connected to the main body in a detachable manner; and calibration means installed in the main body for retrieving data corresponding to the probe means connected to the main body from the stored data in the data storage means and, based on the retrieved data, calibrating at least the receiving channel parameter for each of the plurality of receiving sections of the reception system.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

Figure 1:
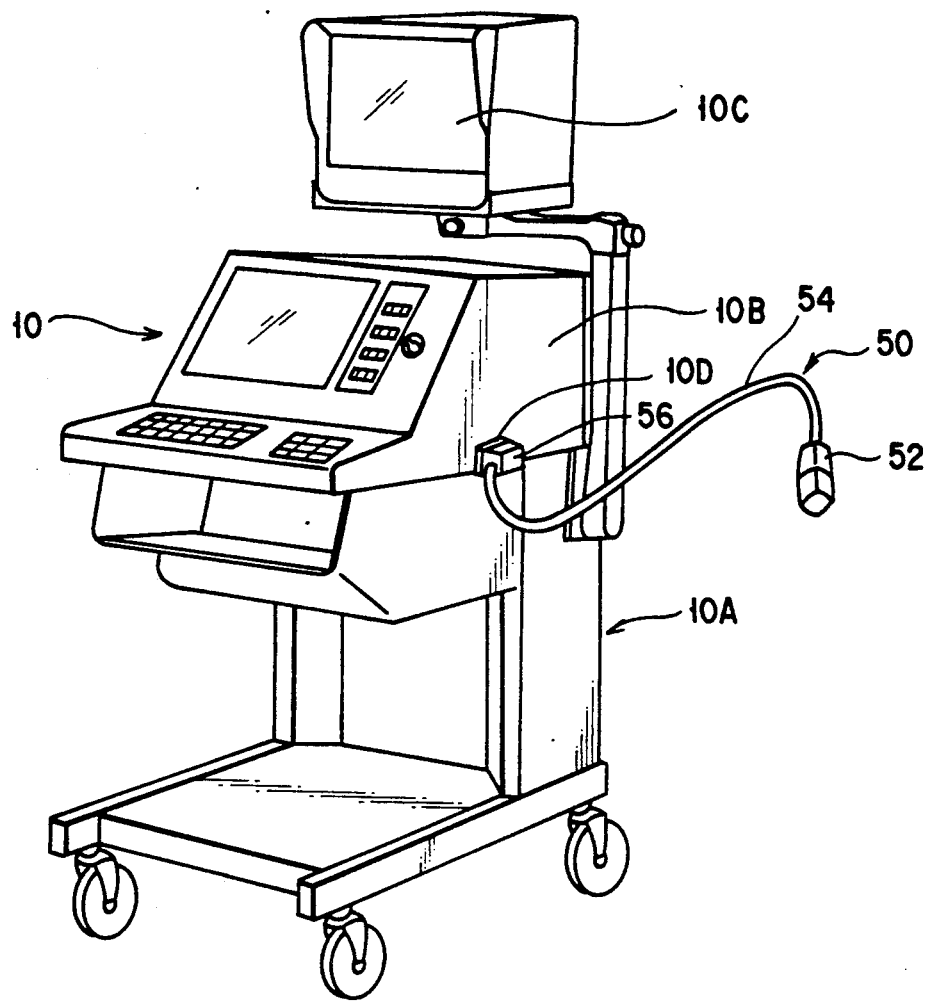
FIG. 1 is a perspective view depicting the appearance of a medical electronic-scanning ultrasonic diagnostic apparatus.

A typical example of the ultrasonic imaging apparatus according to the present invention is a medical electronic-scanning ultrasonic diagnostic apparatus, which is composed of the main body 10 and a probe 50 as shown in FIG. 1.

The main body 10 is made up of a transmission system, a reception system, a signal processing system, a display system including a CRT 10C, all of which are not shown here, and a connector socket section 10D, which are all housed in a casing 10B installed on a truck 10A. At least the transmission system and reception system are electrically connected to the connector socket section 10D.

Figure 2:
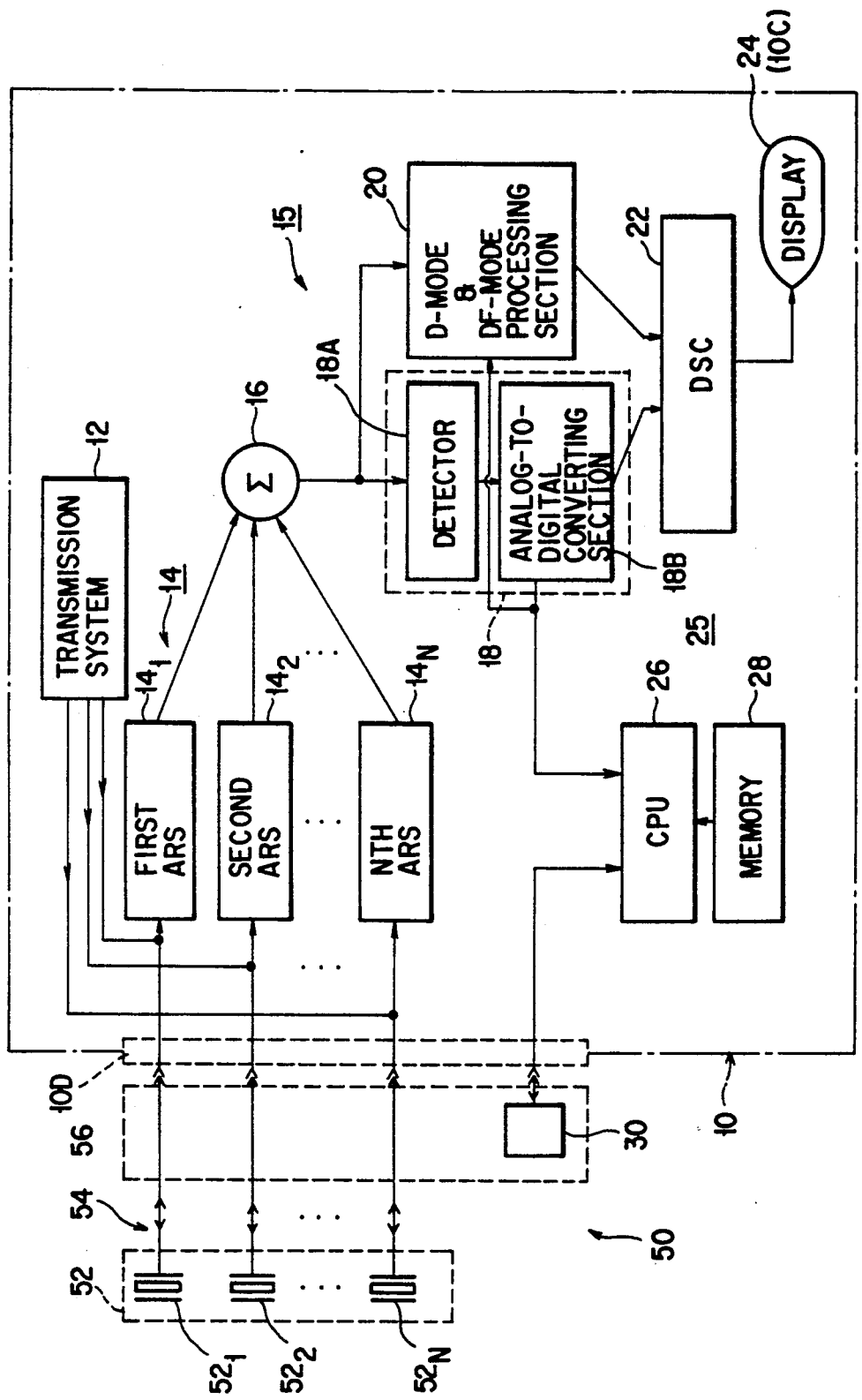
FIG. 2 is a block diagram for an analog reception delay-type medical electronic-scanning ultrasonic diagnostic apparatus according to a first embodiment of the present invention.
Figure 3:
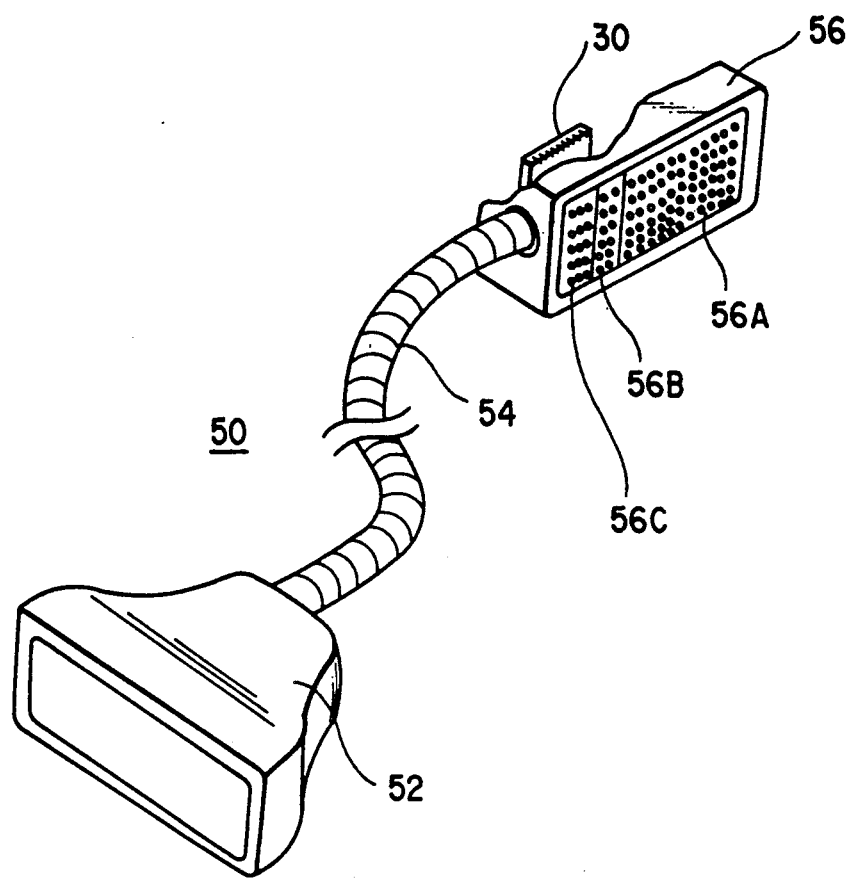
FIG. 3 is a perspective view for the probe unit of the first embodiment.

The probe unit 50, as shown in FIGS. 1, 2, and 3, is composed of a transducer section 52 consisting of an array of N transducers $52_1, 52_2, \ldots, 52_N$, a multicore cable section 54 one end of which is electrically connected to the transducer section 52, and a connector plug section 56 to which the other end of the multicore cable section 54 is electrically connected. In the connector plug section 56, which is connected to the connector socket section 10D in a detachable manner, a semiconductor memory element 30 is installed. The contacts (pins) of the connector plug section 56 is made up of transducer pins 56A for transmission pulses and reception signals, control signal pins 56B for receiving the control signal for a control circuit installed in the connector plug section 56 or transducer section 52 as required, and calibration data pins 56C for calibration data exchange.

As shown in FIG. 2, the main body 10 is composed of a transmission system 12, an analog reception system 14, a signal processing system 15 essentially consisting of an summing circuit 16, a B-mode and M-mode processing section 18, a D-mode and DF-mode processing section 20, and a DSC 22, a display system 24 containing the CRT 10D, a calibration system 25 made up of a CPU 26 and a memory 28, and the connector socket section 10D. This medical electronic-scanning ultrasonic diagnostic apparatus is of the analog reception delay type.

The transmission system 12 supplies pulse voltages to the transducers $52_1, 52_2, \ldots, 52_N$ for ultrasonic transmission, with each voltage assigned a particular delay. Such delay control achieves the convergence and deflection of a transmitted ultrasonic beam.

Figure 4:
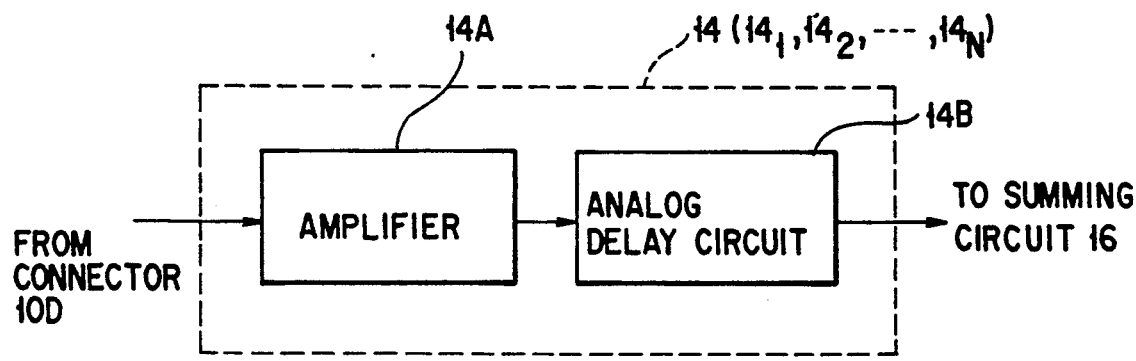
FIG. 4 is a detailed block diagram for a receiving section of the reception system of FIG. 2.

The analog reception system 14 is composed of a first analog receiving section (FIRST ARS) $14_1$, a second analog receiving section $14_2, \ldots,$ and an Nth analog receiving section $14_N$, all of which have the same characteristics. That is, the number of analog receiving sections of the analog reception system is the same as that of transducers of the probe unit 50 and the former are connected to the latter on a one-to-one basis. Such a circuit configuration is normally found in an ultrasonic diagnostic apparatus based solely on sector electronic scanning. In general linear electronic-scanning ultrasonic diagnostic apparatus, the number of transducers is much larger than that of receiving sections. Therefore, a circuit arrangement is provided which allows a plurality of transducers of the transducer section to be connected to the receiving section via a selector. This transducer selecting control enables an ultrasonic beam to move linearly. Here, an explanation will be given about an analog receiving section 14, referring to FIG. 4. The analog receiving section 14 is made up of an amplifier 14A and an analog delay circuit 14B. The amplifier 14A receives the reception signal from a transducer via the connector socket section 10D and amplifies it. The analog delay circuit 14B delays the reception signal amplified at the amplifier 14A for a particular period of time and supplies the resulting signal to a subsequent circuit.

The summing circuit 16 adds the delayed reception signals from the individual transducers $52_1, 52_2, \ldots, 52_N$ of the receiving section 14.

Figure 5:
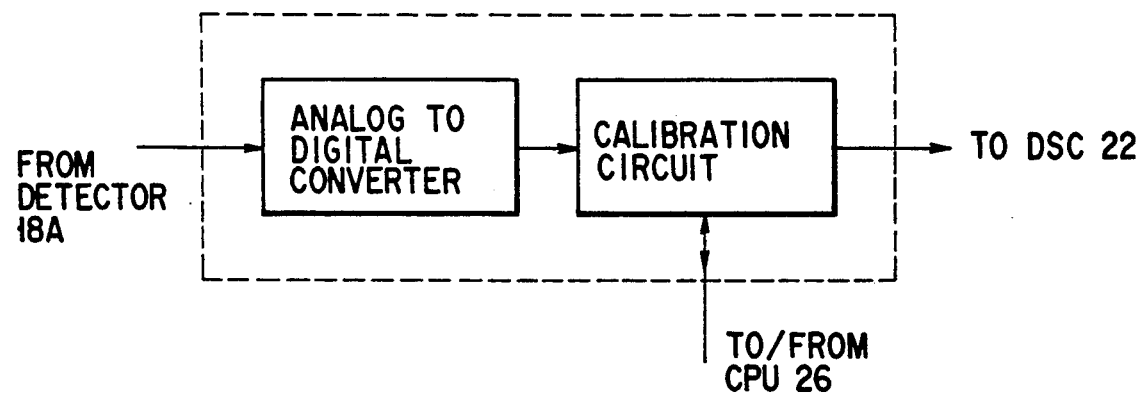
FIG. 5 is a detailed block diagram for the analog-to-digital converting section of FIG. 2.

The B-mode and M-mode processing section 18 of the signal processing system 15 is composed of a detector 18A and an analog-to-digital converting section 18B. The detector 18A receives the summed reception signal from the summing circuit 16 and performs envelope detection of the signal. The analog-to-digital converting section 18B, as shown in FIG. 5, is made up of an analog-to-digital converter $18B_1$ and a calibration circuit $18B_2$. The analog-to-digital converter $18B_1$ converts the analog signal detected at the detector 18A into digital data. To improve the characteristics of the receiving channel parameters, the calibration circuit $18B_2$ calibrates the data from the analog-to-digital converter $18B_1$ on the basis of the calibration data given by the CPU 26 explained later. Improvement of the characteristics of the receiving channel parameters means equalizing at least one of the phase and sensitivity characteristics between the receiving channels.

The D-mode and DF-mode processing section 20 of the signal processing system 15 receives the summed reception signal from the summing circuit 16 and detects the signal to produce a color flow mapping image for Doppler image and BDF mode display (a superposed display of a tomographic image and a color flow mapping image) or MDF-mode display (a superposed display of a motion image and a color flow mapping image). This D-mode and DF-mode processing section 20 also contains a calibration circuit (not shown) similar to the calibration circuit $18_2$ in the B-mode and M-mode processing section 18. To improve the characteristics of the receiving channel parameters, the calibration circuit calibrates the digital data produced at the D-mode and DF-mode processing section 20 on the basis of the calibration data given by the CPU 26 explained later. Improvement of the characteristics of the receiving channel parameters means equalizing at least one of the phase and sensitivity characteristics between the receiving channels.

The DSC 22 of the signal processing system 15 performs scan conversion of the ultrasonic information in the ultrasonic scan form obtained at the B-mode and M-mode processing section 18 and the D-mode and DF-mode processing section 20 into image information in, for example, the standard TV scan form. In carrying out scan conversion, the DSC 22 also performs image synthesis to provide B-mode display (tomographic image display), M-mode display (motion image display), D-mode display (Doppler image display), BDF-mode display (superposed display of a tomographic image and a flow mapping image), and MDF-mode display (superposed display of a motion image and a color mapping image) according to the clinical and/or technical conditions that the operator wants.

The display system 24 including the CRT 10D displays various images.

The calibration system 25 retrieves calibration data from a semiconductor memory element 30 installed in the connector plug 56 to calibrate the receiving channel parameters for the reception system 14. It also retrieves standard data from the memory 28, such as a semiconductor memory element, flexible magnetic floppy disk, or hard magnetic disk, to calibrate the receiving channel parameters for the reception system 14.

The CPU 26 of the calibration system 25 receives measurement data from the analog-to-digital converting section 18B to produce calibration data. The measurement data undergoes a specific processing at the CPU 26 and the processed data is stored as calibration data in the semiconductor memory element 30 in the connector plug 56 via the connector socket 10D and connector plug 56.

Therefore, the calibration data stored in the semiconductor memory element 30 is similar to the standard data stored in the memory 28 in that data containing transducer channel parameters (at least one of the sensitivity level and phase difference), which differ from one probe unit to another, and the receiving channel parameters (at least one of the sensitivity level and phase difference) is represented in the form of digital data. However, they are different from each other in that the calibration data is obtained by actual measurement, while the standard data is obtained by actual measurement or simulation, and that the calibration data can be changed whenever necessary, whereas the standard data can remain unchanged.

Figure 6:
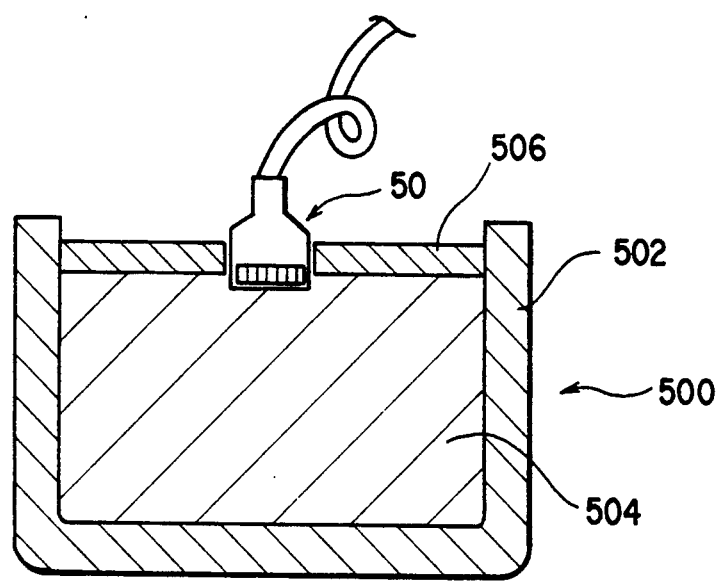
FIG. 6 is a sectional view of a device for measuring the phase and sensitivity characteristics of the probe unit.

In addition to the above method, the calibration or standard data can be obtained using a device 500 shown in FIG. 6. In the data acquisition device 500, an ultrasonic medium 504 such as water is retained in a box container 502 made of, for example, acrylic acid resin, and a probe fixture 506 made of, for example, acrylic acid resin, is attached to the box container 502. The probe fixture 506 has a hole in it, into which the end of the probe 50 serving as the ultrasonic transmitting and receiving surface is fitted.

Figure 7:
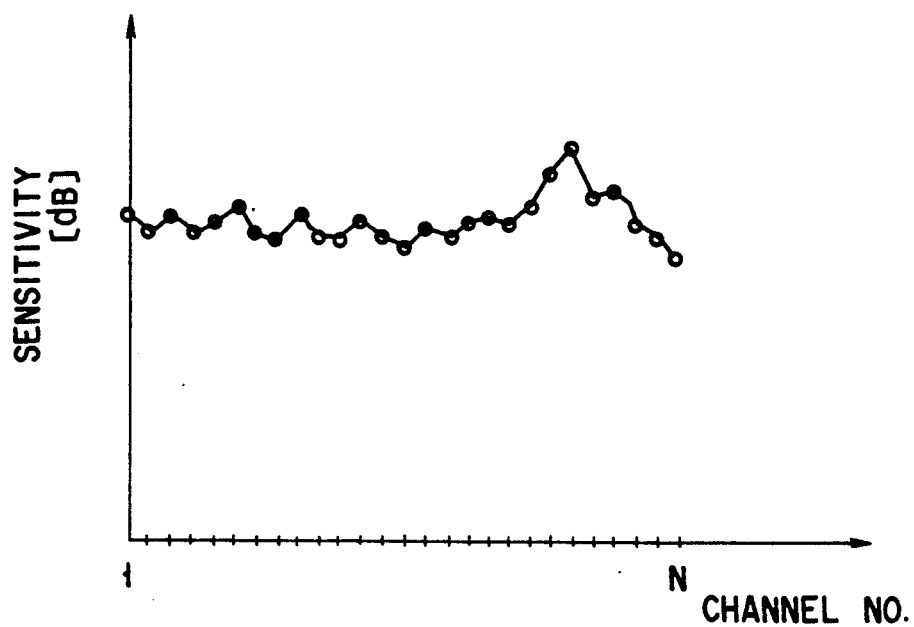
FIG. 7 is a graph representing the relationship between the channel number of the transducer and the sensitivity level.
Figure 8:
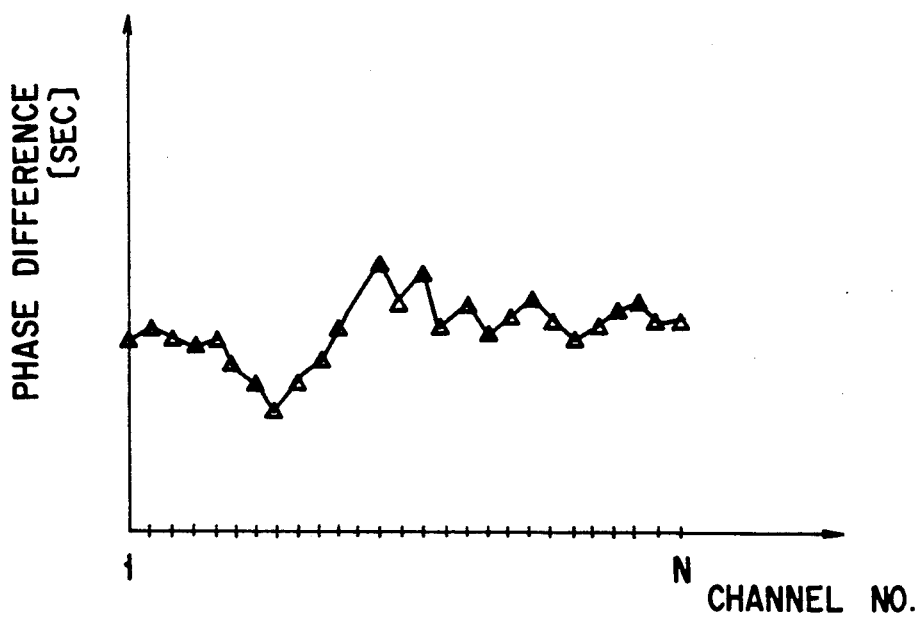
FIG. 8 is a graph representing the relationship between the channel number of the transducer and the phase difference.

With the probe unit 50 attached to the data acquisition device 500, the main body 10 is activated. The transmission system 12 drives the first transducer $52_1$ through transmission, and the resulting data goes into the CPU 26 via the signal processing system 15. Similarly, the transmission system 12 then drives the second transducer $52_2$, and the resulting data is supplied to the CPU 26. This action is repeated until data on the Nth transducer $52_N$ is supplied to the CPU 26. As a result, the characteristics of sensitivity level and phase difference for each transducer channel are obtained as shown in FIGS. 7 and 8, respectively.

After the repetitious action is completed, the CPU 26, based on the data on the individual transducers, produces data representing the characteristics of at least one of sensitivity level and phase difference between transducer channels and between receiving channels, and then writes the resulting data as calibration data into the semiconductor memory element 30. For another probe unit 50, it also writes calibration data into the semiconductor memory element 30 in the same manner.

In the first embodiment, with one probe unit 50 connected to the main body 10, the receiving channel parameters are calibrated on the basis of the transducer channel parameters for the one probe unit 50. With the other probe unit 50 connected to the main body 10, the receiving channel parameters are calibrated on the basis of the transducer channel parameters for the other probe unit 50. This enables appropriate parameter setting for each probe unit 50 used, thereby providing a good ultrasonic image.

In the above example, the probe unit 50 is provided with calibration data, whereas in a second embodiment shown in FIGS. 9 and 10, which will be explained in detail below, the main body 10 is provided previously with calibration data for each of a plurality of probe units 50 to be used. That is, with the first embodiment, calibration data necessary for use of a probe unit with the main body is transferred directly to the main body by connecting the probe unit 50 to the main body 10.

The second embodiment is less simple than the first embodiment. Because the main body has calibration data in it, just connecting the probe unit 50 to the main body 10 cannot select the necessary pieces of calibration data from a large amount of calibration data.

In the second embodiment, therefore, the connector plug 56 of the probe unit 50 is provided with a circuit generating probe identifying information. With this arrangement, connecting the probe unit 50 to the main body 10 enables probe identifying information to be transferred to the main body 10, which makes it possible to easily select the necessary pieces of calibration data for the use of the probe unit 50 with the main body 10 from a large amount of calibration data previously stored in a memory such as a magnetic disk.

Figure 9:
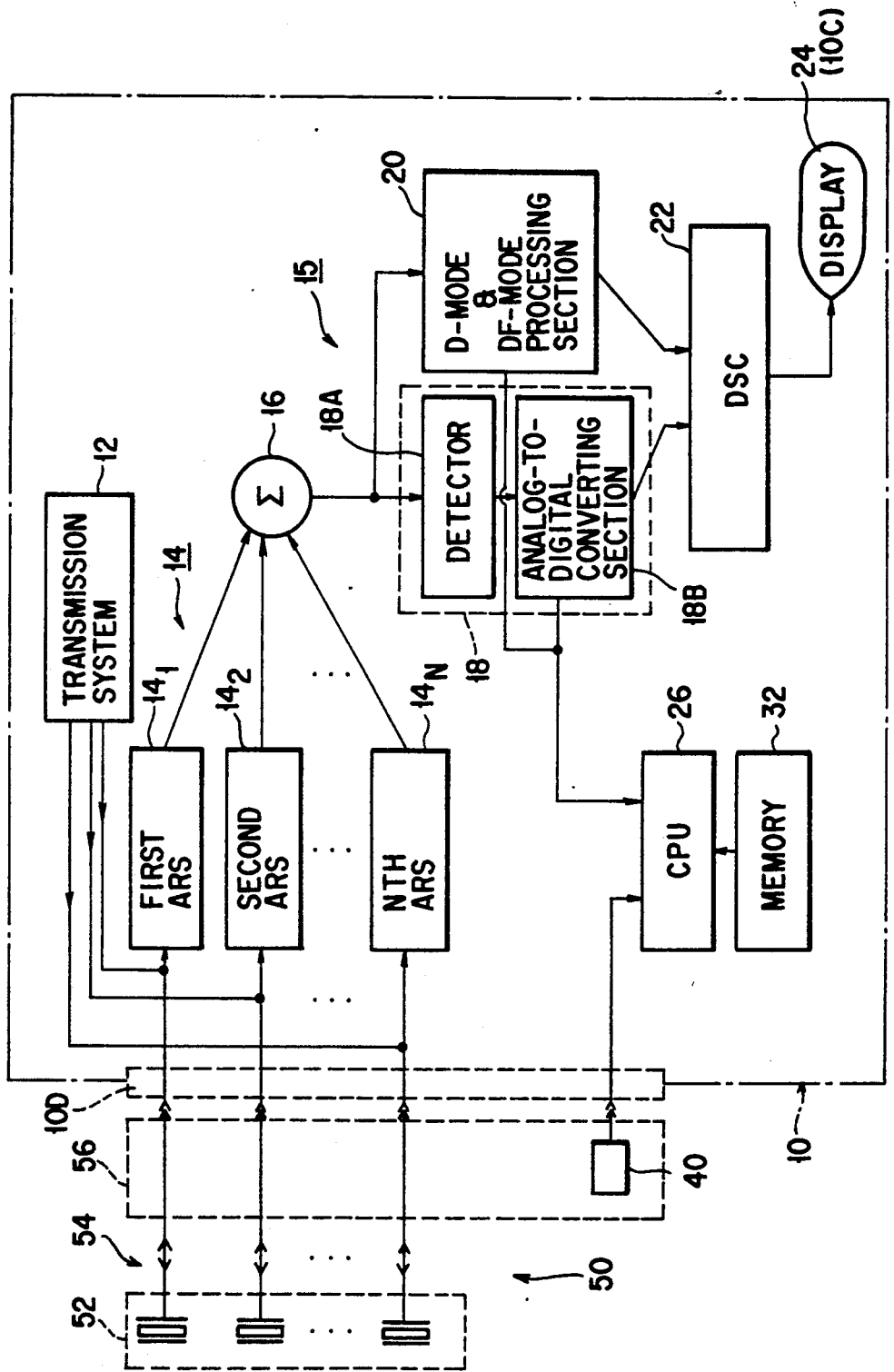
FIG. 9 is a block diagram for an analog reception delay-type medical electronic-scanning ultrasonic diagnostic apparatus according to a second embodiment of the present invention.
Figure 10:
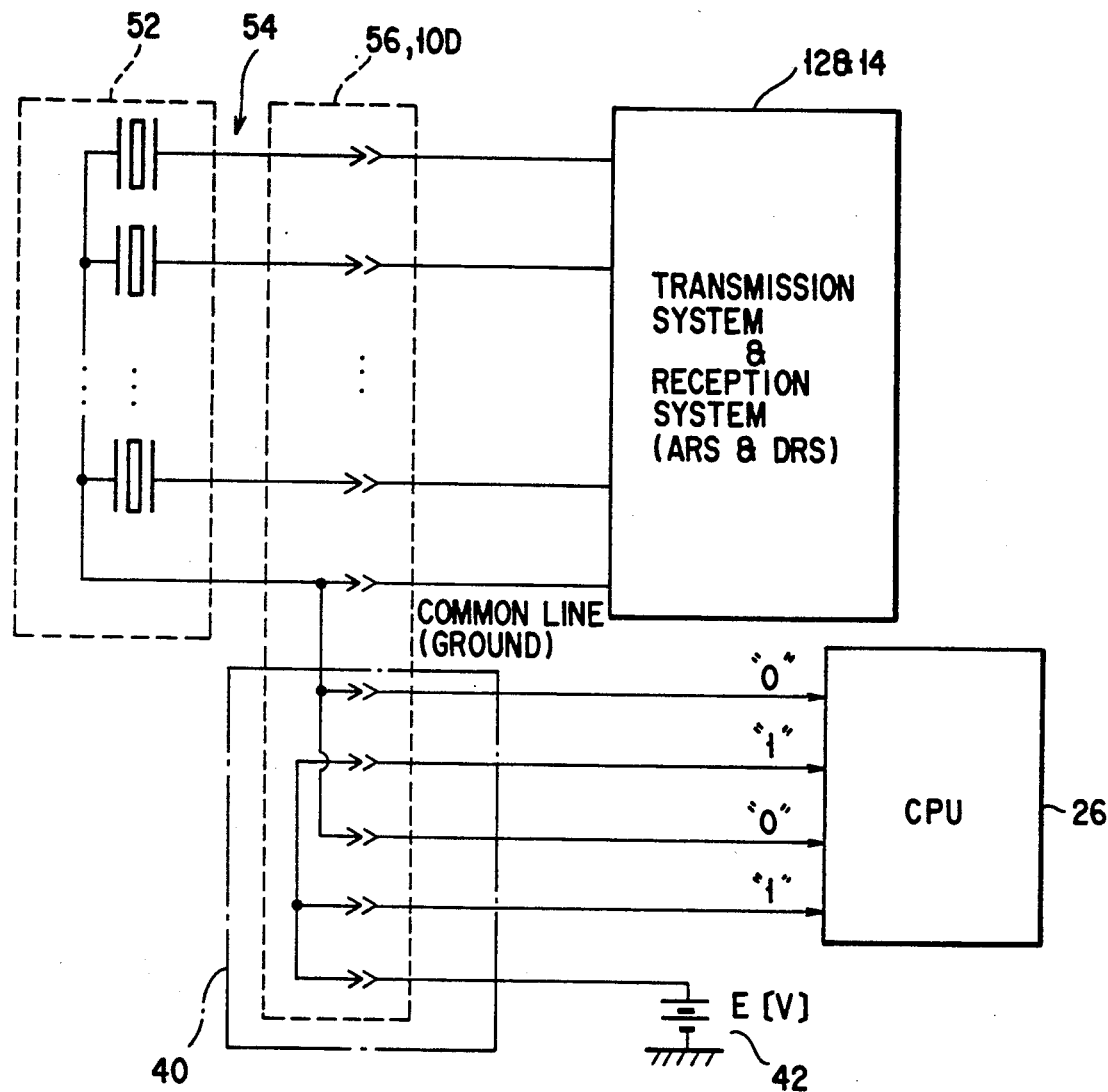
FIG. 10 is a block diagram of a circuit for producing a probe identifying data that is to be supplied from the probe unit to the main body.

FIG. 9 shows an analog reception delay-type medical electronic-scanning ultrasonic diagnostic apparatus according to the second embodiment of the present invention. A memory 32 is a memory medium such as a semiconductor memory element, magnetic floppy disk, or hard magnetic disk. The memory 32 retains the calibration data and standard data as explained in the first embodiment.

The probe identifying data generating circuit 40 can be constructed just by combining a plurality of signal lines with the connector plug 56 of the probe unit 50 and providing the main body 10 with a power supply 42. That is, connecting the connector plug 56 of the probe unit 50 to the connector socket 100D of the main body 10 allows 4 bits of probe identifying data "0101" to be transferred to the CPU 26. The calibration data corresponding to the probe identifying data "0101" is retrieved from the memory 32. Based on the calibration data, calibration is carried out provided that a specific piece of probe identifying data has been assigned beforehand to a piece of calibration data for each probe unit 50 previously stored in the memory 32.

Figure 11:
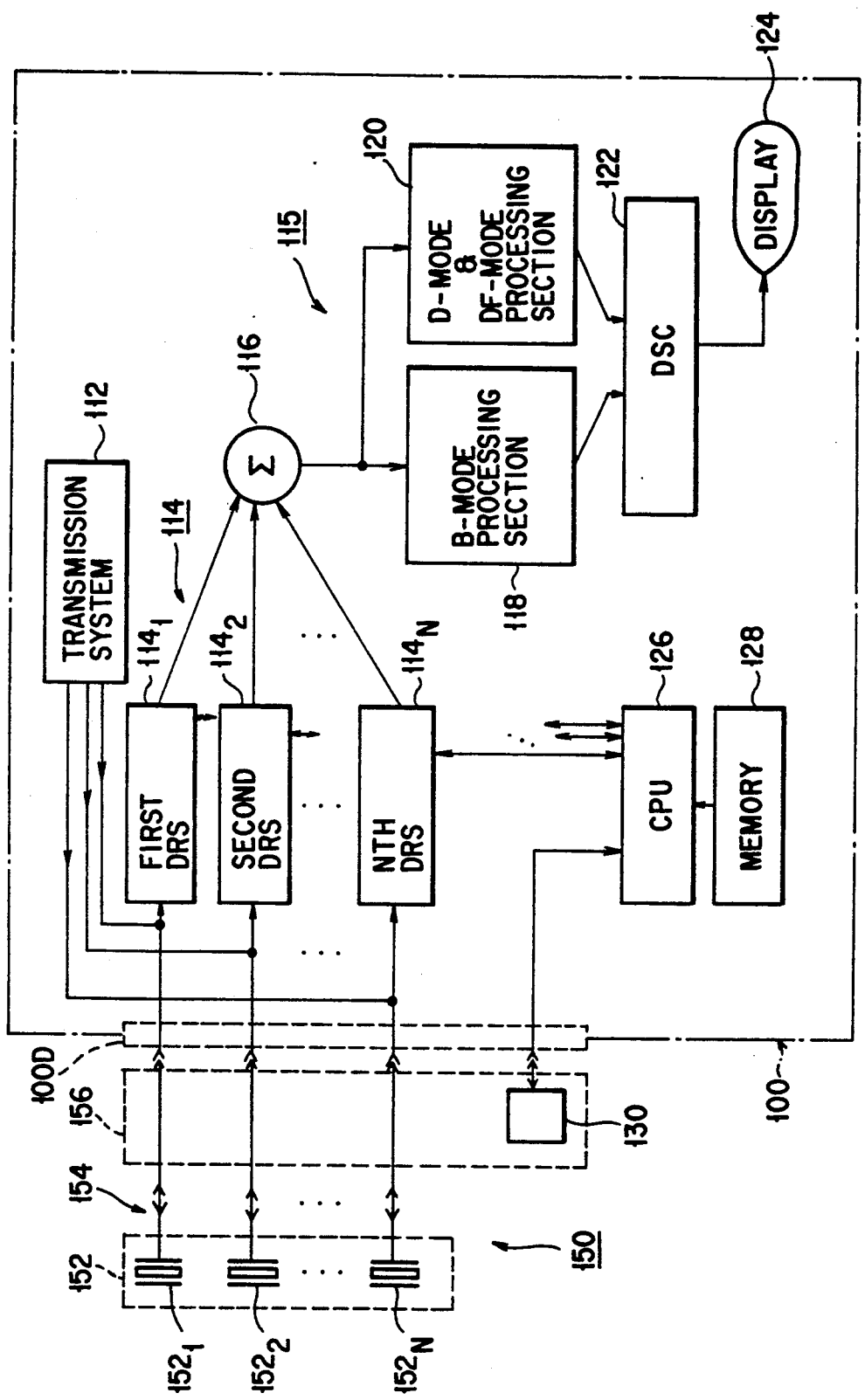
FIG. 11 is a block diagram for a digital reception delay-type medical electronic-scanning ultrasonic diagnostic apparatus according to a third embodiment of the present invention.
Figure 12:
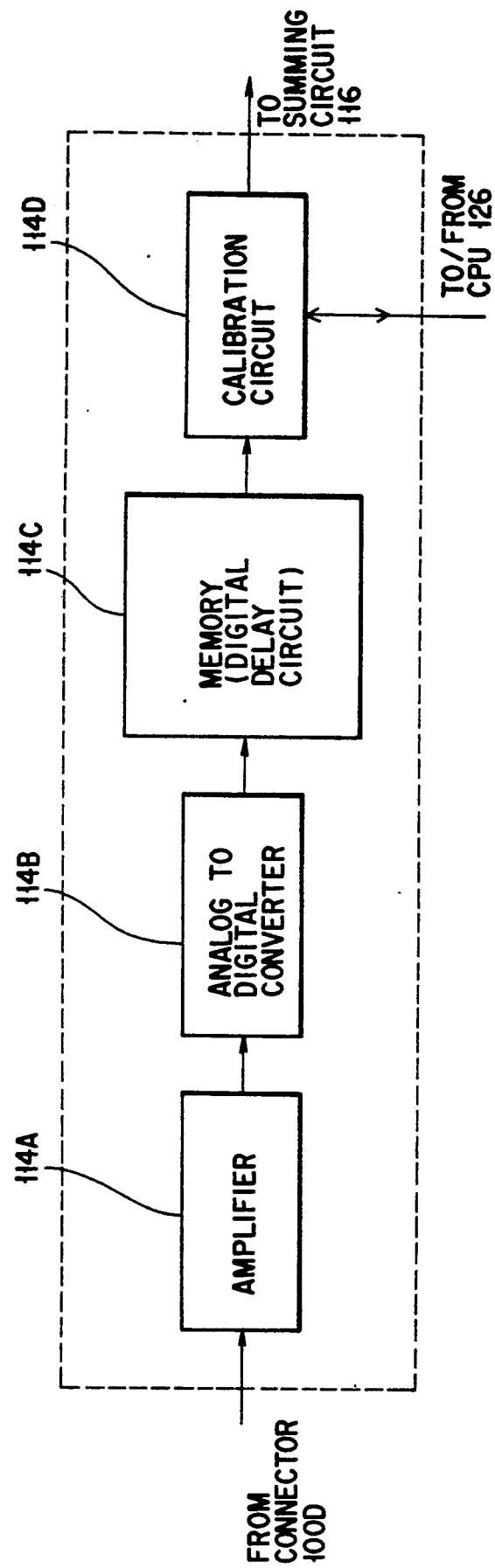
FIG. 12 is a detailed block diagram for a receiving section of the digital reception system of FIG. 11.
Figure 13:
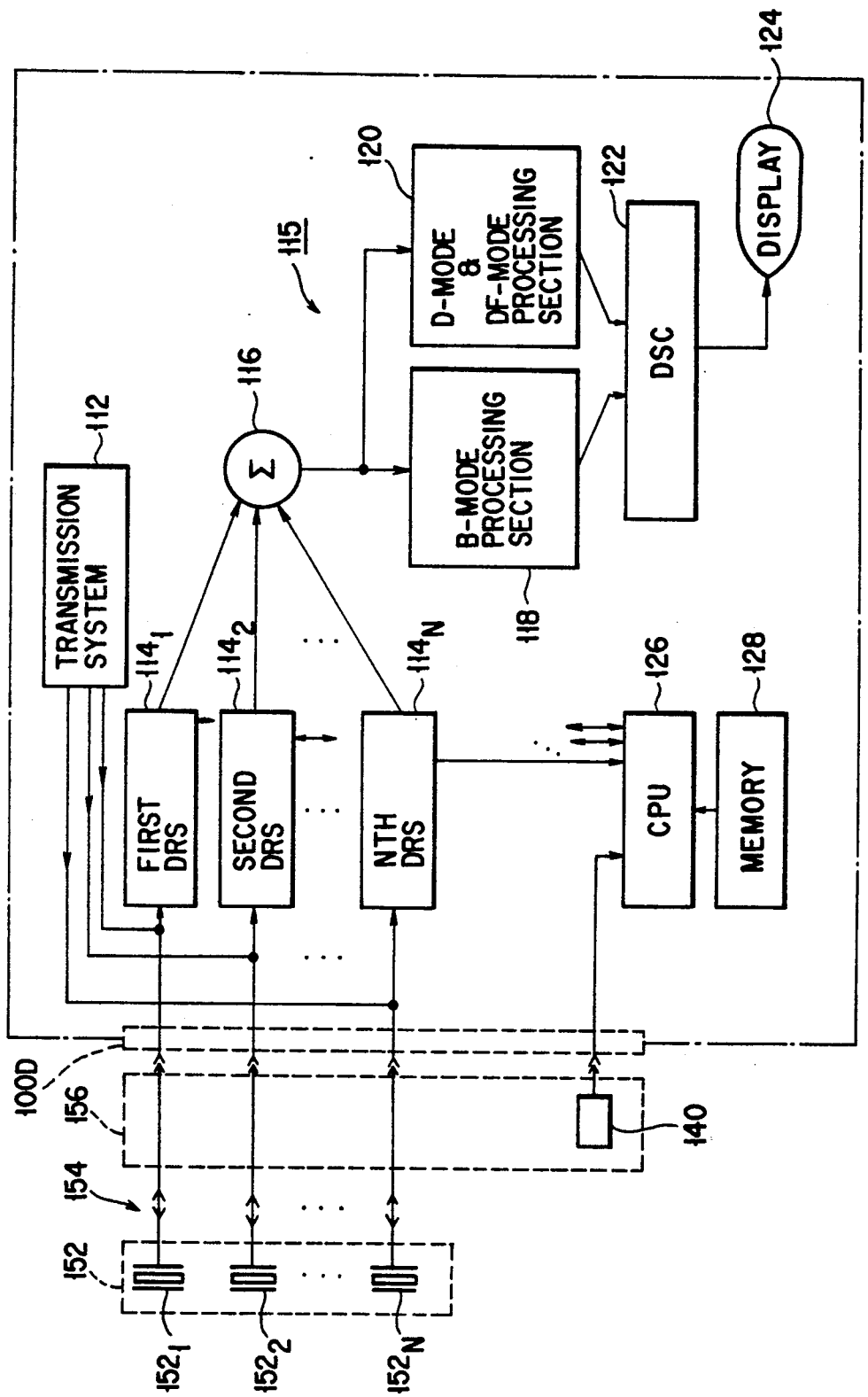
FIG. 13 is a block diagram for a digital reception delay-type medical electronic-scanning ultrasonic diagnostic apparatus according to a fourth embodiment of the present invention.

While the aforementioned the first and second embodiments are analog reception delay-type medical electronic-scanning ultrasonic diagnostic apparatus, a third and fourth embodiments shown in FIGS. 11 through 13 are digital reception-type medical electronic-scanning ultrasonic diagnostic apparatus.

As shown in FIG. 11, the main body 100 is composed of a transmission system 102 basically the same as those of the first and second embodiments, a digital reception system 104, a signal processing system 115 basically consisting of a summing circuit 106, a B-mode and M-mode processing section 108, a D-mode and DF-mode processing section 120, and a DSC 122, a display system 124 containing the CRT 110D, a calibration system 125 made up of a CPU 126 and a memory 128, and the connector socket section 100D. The probe unit 150 is apparently the same as those in FIGS. 1 and 3. That is, the probe unit 150 is composed of a transducer section 152 consisting of an array of N transducers $152_1$, $152_2$, ..., $152_N$, a multicore cable section 154 one end of which is electrically connected to the transducer section 152, and a connector plug section 156 to which the other end of the multicore cable section 154 is electrically connected. In the connector plug section 156, which is connected to the connector socket section 100D in a detachable manner, a semiconductor memory element 130 is installed.

The transmission system 112 supplies pulse voltages to the transducers $152_1$, $152_2$, ..., $152_N$ for ultrasonic transmission, with each voltage assigned a particular delay. Such delay control achieves the convergence and deflection of a transmitted ultrasonic beam.

The digital reception system 114 is composed of a first digital receiving section (FIRST ADS) $114_1$, a second digital receiving section $114_2$, ..., and an Nth digital receiving section $114_N$, which all have the same characteristics. That is, the number of digital receiving sections of the digital reception system 114 is the same as that of transducers of the prove unit 150 and the former are connected to the latter on a one-to-one basis. Such a circuit configuration is normally found in an ultrasonic diagnostic apparatus based solely on sector electronic scanning. In general linear electronic-scanning ultrasonic diagnostic apparatus, the number of transducers is much larger than that of receiving sections. For this reason, a circuit arrangement is provided which allows a plurality of transducers of the transducer section to be connected to the receiving section via a selector. This transducer selecting control enables linear movement of an ultrasonic beam. Here, a digital receiving section 114 will be explained, referring to FIG. 12. The digital receiving section 114 is made up of an amplifier 114A, an analog-to-digital converter 114B, a memory 114C made up of a semiconductor memory element acting as a digital delay circuit, and a calibration circuit 114D. The digital delay circuit 114C essentially effects reception delay control by adjusting the timing of write and read into and from the semiconductor memory element. The amplifier 114A receives the reception signal from a transducer via the connector socket section 100D and amplifies it. The digital delay circuit 114 delays for a particular period of time the reception signal amplified at the amplifier 114A and digitized at the analog-to-digital converter 114B and supplies the resulting signal to the calibration circuit 114D at a subsequent stage. To improve the characteristics of the receiving channel parameters, the calibration circuit 114D calibrates the data from the digital delay circuit 114C on the basis of the calibration data given by the CPU 126 explained later. Improvement of the characteristics of the receiving channel parameters means equalizing at least one of the phase and sensitivity characteristics between the receiving channels.

The summing circuit 116 adds the delayed reception signals from the individual transducers $152_1$, $152_2$, ..., $152_N$ of the receiving section 114.

The B-mode and M-mode processing section 118 of the signal processing system 115 receives the summed reception signal from the summing circuit 116 and performs envelope detection of the signal in a digital manner.

The D-mode and DF-mode processing section 120 of the signal processing system 115 receives the summed reception signal from the summing circuit 116 and detects the signal to produce a color flow mapping image for Doppler image and BDF mode display (a superposed display of a tomographic image and a color flow mapping image) or MDF-mode display (a superposed display of a motion image and a color flow mapping image).

The DSC 122 of the signal processing system 115 performs scan conversion of the ultrasonic information in the ultrasonic scan form obtained at the B-mode and M-mode processing section 118 and the D-mode and DF-mode processing section 120 into image information in, for example, the standard TV scan form. In carrying out scan conversion, the DSC 122 also performs image synthesis to provide B-mode display (tomographic image display), M-mode display (motion image display), D-mode display (Doppler image display), BDF-mode display (superposed display of a tomographic image and a flow mapping image), and MDF-mode display (superposed display of a motion image and a color mapping image) according to the clinical and/or technical conditions that the operator wants.

The display system 124 including the CRT 100D displays various images generated at the DSC 122.

The calibration system 125 retrieves calibration data from the semiconductor memory element 130 installed in the connector plug 156 to calibrate the receiving channel parameters for the reception system 114. It also retrieves standard data from the memory 128, such as a semiconductor memory element, flexible magnetic floppy disk, or hard magnetic disk, to calibrate the receiving channel parameters for the reception system 114.

The CPU 126 of the calibration system 125 receives measurement data from the digital-to-digital converting section 118B to produce calibration data. The measurement data undergoes a specific processing at the CPU and the processed data is stored as calibration data in the semiconductor memory element 130 in the connector plug 156 via the connector socket 100D and connector plug 156.

Therefore, the calibration data stored in the semiconductor memory element 130 is similar to the standard data stored in the memory 128 in that data containing transducer channel parameters (at least one of the sensitivity level and phase difference), which differ from one probe unit to another, and the receiving channel parameters (at least one of the sensitivity level and phase difference) is represented in the form of digital data. However, they are different from each other in that the calibration data is obtained by actual measurement, while the standard data is obtained by actual measurement or simulation, and that the calibration data can be changed whenever necessary, whereas the standard data can remain unchanged.

With the above arrangement, based on the data on the individual transducers, the CPU produces data representing the characteristics of at least one of sensitivity level and phase difference between transducer channels and between receiving channels, and then writes the resulting data as calibration data into the semiconductor memory element 130. For another probe unit 150, it also writes calibration data into the semiconductor memory element 130 in the same manner.

In the above third embodiment, with one probe unit 150 connected to the main body 100, the receiving channel parameters are calibrated on the basis of the transducer channel parameters for the one probe unit 150. With the other probe unit 150 connected to the main body 100, the receiving channel parameters are calibrated on the basis of the transducer channel parameters for the other probe unit 150. This allows appropriate parameter setting for each probe unit 150 used, thereby providing a good ultrasonic image.

In the above example, the probe unit 50 is provided with calibration data, whereas in a second example shown in FIGS. 9 and 10, which will be explained in detail below, the main body 10 is provided beforehand with calibration data for each of a plurality of probe units 50 to be used. That is, with the first example, calibration data necessary for use of a probe unit with the main body is transferred directly to the main body through connection of the probe unit 50 to the main body 10.

The second example is less simple than the first example. Because the main body has calibration data in it, just connecting the probe unit 50 to the main body 10 cannot select the necessary pieces of calibration data from a large amount of calibration data.

In the second example, therefore, the connector plug 56 of the probe unit 50 is provided with a circuit generating probe identifying information. With this arrangement, connecting the probe unit 50 to the main body 10 enables probe identifying information to be transferred to the main body 10, which makes it possible to easily select the necessary pieces of calibration data for the use of the probe unit 50 with the main body 10 from a large amount of calibration data previously stored in a memory such as a magnetic disk.

FIG. 9 shows an analog reception delay-type medical electronic-scanning ultrasonic diagnostic apparatus according to a second embodiment of the present invention. A memory 32 is a memory medium such as a semiconductor memory element, magnetic floppy disk, or hard magnetic disk. The memory 32 retains the calibration data and standard data of the first example.

The probe identifying data generating circuit 40 can be constructed just by combining a plurality of signal lines with the connector plug 56 of the probe unit and providing the main body 10 with a power supply 42. That is, connecting the connector plug 56 of the probe unit 50 to the connector socket 100D of the main body 10 allows 4 bits of probe identifying data "0101" to be transferred to the CPU 26. The calibration data corresponding to the probe identifying data "0101" is retrieved from the memory 32. Based on the calibration data, calibration is carried out provided that a specific piece of probe identifying data has been assigned beforehand to a piece of calibration data for each probe unit 50 previously stored in the memory.

Regular calibration of the calibration data and standard data provides much better ultrasonic information.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An ultrasonic imaging apparatus comprising:
   a main body including at least a transmission system, a reception system having a plurality of receiving sections, a signal processing system, a display system, and a first connector;
   probe means including a plurality of transducers;
   a second connector for connecting the probe means to the first connector of the main body in a detachable manner;
   data storage means installed in the second connector for storing data on a transducer channel parameter for each of the plurality of transducers, the transducer channel parameter being at least one of a sensitivity level and a phase difference between transducer channels inherent to the probe means; and
   calibration means installed in the main body for retrieving stored data from the data storage means and for calibrating a receiving channel parameter for each of the plurality of receiving sections of the reception system, the receiving channel parameter being at least one of a sensitivity level and a phase difference between the transducer channels inherent to the reception system.

2. An ultrasonic imaging apparatus according to claim 1, wherein the calibration means includes means for measuring data on the transducer channel parameter for each of the plurality of transducers.

3. An ultrasonic imaging apparatus according to claim 1, wherein the calibration means includes standard data retaining means for retaining standard data on at least one of the transducer channel parameter and the receiving channel parameter.

4. An ultrasonic imaging apparatus according to claim 1, wherein the plurality of receiving sections of the reception system include a plurality of analog receiving sections.

5. An ultrasonic imaging apparatus according to claim 1, wherein the plurality of receiving sections of the reception system include a plurality of digital receiving sections.

6. An ultrasonic imaging apparatus according to claim 1, wherein the probe means includes a transducer section including the plurality of transducers and a cable having one end connected to the transducer section and another end connected to the second connector.

7. An ultrasonic imaging apparatus comprising:
a main body including at least a transmission system, a reception system having a plurality of receiving sections, a signal processing system, and a display system;
probe means including a plurality of transducers, the probe means being connected to the main body in a detachable manner;
data storage means installed in the main body for storing data on a transducer channel parameter for each of the plurality of transducers, the transducer channel parameter being at least one of a sensitivity level and a phase difference between transducer channels inherent to the probe means; and
calibration means installed in the main body for retrieving data corresponding to the probe means connected to the main body from the stored data in the data storage means and, based on the retrieved data, for calibrating at least a receiving channel parameter for each of the plurality of receiving sections of the reception system, the receiving channel parameter being at least one of a sensitivity level and a phase difference between the transducer channels inherent to the probe means.

8. An ultrasonic imaging apparatus according to claim 7, wherein the calibration means includes means for measuring data on the transducer channel parameter for each of the plurality of transducers.

9. An ultrasonic imaging apparatus according to claim 7, wherein the plurality of receiving sections of the reception system include a plurality of analog receiving sections.

10. An ultrasonic imaging apparatus according to claim 7, wherein the plurality of receiving sections of the reception system include a plurality of digital receiving sections.

11. An ultrasonic imaging apparatus according to claim 7, wherein the data storage means is one of a semiconductor memory element, IC card, flexible magnetic floppy disk, and hard magnetic disk.

12. An ultrasonic imaging apparatus according to claim 7, wherein the probe means includes a transducer section including the plurality of transducers, a cable having one end connected to the transducer section, and a connector for connecting another end of the cable to at least the transmission system and reception system, and the connector including means for generating data to identify specifications of the probe means connected to the main body.

* * * * *

UNITED STATES PATENT AND TRADEMARK OFFICE
CERTIFICATE OF CORRECTION

PATENT NO. : 5,251,631
DATED : October 12, 1993
INVENTOR(S) : Masayoshi Tsuchiko et al.

It is certified that error appears in the above-indentified patent and that said Letters Patent is hereby corrected as shown below:

Abstract, title page, line 8, change "in stalled" to --installed--.

Signed and Sealed this

Twentieth Day of September, 1994

Attest:

BRUCE LEHMAN

*Attesting Officer*        *Commissioner of Patents and Trademarks*